US011039783B2

(12) United States Patent
Kochura et al.

(10) Patent No.: US 11,039,783 B2
(45) Date of Patent: Jun. 22, 2021

(54) AUTOMATIC CUEING SYSTEM FOR REAL-TIME COMMUNICATION (71) Applicant: International Business Machines Corporation, Armonk, NY (US)

(72) Inventors: Nadiya Kochura, Bolton, MA (US); Fang Lu, Billerica, MA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/011,192

(22) Filed: Jun. 18, 2018

(65) Prior Publication Data
US 2019/0380643 A1 Dec. 19, 2019

(51) Int. Cl.
*G10L 17/26* (2013.01)
*A61B 5/00* (2006.01)
*A61B 5/02* (2006.01)
*A61B 5/16* (2006.01)
*G16H 10/60* (2018.01)

(52) U.S. Cl.
CPC .............. *A61B 5/4803* (2013.01); *A61B 5/02* (2013.01); *A61B 5/165* (2013.01); *G16H 10/60* (2018.01); *G10L 17/26* (2013.01)

(58) Field of Classification Search
CPC .............................. G06F 17/3053; G10L 17/26
See application file for complete search history.

(56) References Cited

U.S. PATENT DOCUMENTS

| 7,401,020 | B2 | 7/2008 | Eide |
| 9,493,130 | B2 | 11/2016 | Penilla et al. |
| 9,542,695 | B2 | 1/2017 | Russell et al. |
| 9,754,229 | B2 | 9/2017 | Romanoff et al. |
| 2005/0071163 | A1 | 3/2005 | Aaron et al. |
| 2009/0002178 | A1* | 1/2009 | Guday ................. G06F 3/0346 340/573.1 |

(Continued)

FOREIGN PATENT DOCUMENTS

CN 110618804 A 12/2019

OTHER PUBLICATIONS

Northrup Grumman; "Understanding Voice and Data Link Networking"; Northrup Grumman's Guide to Secure Tactical Data Links, Dec. 2014.

(Continued)

*Primary Examiner* — Feng-Tzer Tzeng
(74) *Attorney, Agent, or Firm* — Reza Sarbakhsh (57) ABSTRACT A method, system and computer program product for providing an automatic cueing system for real-time communication, by: collecting a first person's profile data, which may include a medical history, to determine how the first person reacts to different voice or audio characteristics and sounds; analyzing the first person's voice or audio characteristics and sounds to categorize a current condition of the first person; and then dynamically adjusting voice or audio characteristics and sounds of responses made to the first person by a robotic device or a second person, based on the first person's profile data and the current condition of the first person. Thereafter, the first person's voice or audio characteristics and sounds, as well as the responses made to the first person, may be continuously monitored, along the first person's vital signs, to update the current condition of the first person.

20 Claims, 4 Drawing Sheets (56) References Cited

U.S. PATENT DOCUMENTS

2016/0104486 A1* 4/2016 Penilla .................. G10L 15/005
                                                    704/232
2016/0154889 A1* 6/2016 Allen .................... G06F 16/335
                                                    707/728

OTHER PUBLICATIONS

IBM; "Automatic Monitoring Audience and Presenter in Presentations with Cues to Improve Delivery Technique", http://ip.com/IPCOM/000184881D, Jul. 3, 2009.
Anonymously; "Echo Caller When Muted"; http://ip.com/IPCOM/000206949D; May 13, 2011.
Motorola et al., "Automatic Voice Response to DTMF Tone Conversion"; http://ip.com/IPCOM/000004634D; Mar. 7, 2001.
"You Had Me at Hello—Why Customer Service Tone Matters in Contact Center Communications", www.virtualhold.com/blog/hello-voice-tone-matters-call-center-communications/, as downloaded Jun. 11, 2018.
Zoom Blog, "Using Speech Analytics in Call Center Agent Training", Published Sep. 2, 2015, 11 pages, https://blog.zoomint.com/blog/using-speech-analytics-in-call-center-agent-training.
Mell, et al., "The NIST Definition of Cloud Computing", National Institute of Standards and Technology, Special Publication 800-145, Sep. 2011, 7 pages.

* cited by examiner

AUTOMATIC CUEING SYSTEM FOR REAL-TIME COMMUNICATION

BACKGROUND

The present invention relates generally to a method and system for automatic cueing for real-time communication.

Along with fast evolving technology, more and more artificial intelligence (AI) based devices are integrated into everyone's day-to-day lives.

For example, in a busy hospital emergency room (ER) setting, a cognitive-analysis-enabled robotic device can be used to provide initial triage tasks when new patients check-in. However, it is important for the robotic device to use a proper voice tone to communicate with the new patients to make sure they feel as much as ease as possible. This will help eliminate any biased factors in the evaluation of the new patients.

In another example, in a healthcare call center, employees are responsible for interacting with patients or customers, medical companies, insurers, and others in the industry. The employees of the healthcare call center are expected to provide customer service while increasing productivity. Again, it is important for the employees to use a proper voice tone to communicate with the patients or customers to make sure they feel as much as ease as possible.

The article, www.virtualhold.com/blog/hello-voice-tone-matters-call-center-communications/, provides some general background information that describes why it is important for employees to use a proper voice tone when working in a healthcare call center. Often, a person's emotional state is communicated by their voice tone. Consequently, voice tone can be categorized as positive, such as sincere, friendly and professional, or negative, such as less enthusiastic and dismissive.

Thus, there is a need in the art for a mechanism to promote proper voice tone for robotic devices and employees when interacting with others.

SUMMARY

The invention provided herein has many embodiments useful, for example, in implementing a method, system and computer program product for providing an automatic cueing system for real-time communication with a first person, by: collecting the first person's profile data, which may include a medical history, to determine how the first person reacts to different voice or audio characteristics and sounds; analyzing the first person's voice or audio characteristics and sounds to categorize a current condition of the first person; and dynamically adjusting voice or audio characteristics and sounds of responses made to the first person, based on the first person's profile data and the current condition of the first person, to ensure that the current condition of the first person stays within a desired range. Thereafter, the first person's voice or audio characteristics and sounds, as well as the responses made to the first person, may be continuously monitored, along the first person's vital signs, to update the current condition of the first person.

In one embodiment, the automatic cueing system controls at least one robotic device to dynamically adjust the voice or audio characteristics and sounds of the responses made by the robotic device to the first person. In another embodiment, the automatic cueing system provides visual and/or audio cues to a second person to dynamically adjust the voice or audio characteristics and sounds of the responses made by the second person to the first person.

BRIEF DESCRIPTION OF THE DRAWINGS

Referring now to the drawings in which like reference numbers represent corresponding parts throughout.

DETAILED DESCRIPTION

In the following description, reference is made to the accompanying drawings which form a part hereof, and in which is shown by way of illustration one or more specific embodiments in which the invention may be practiced. It is to be understood that other embodiments may be utilized and structural and functional changes may be made without departing from the scope of the present invention.

Overview

The present invention provides for an automatic cueing system for real-time communication. Specifically, the automatic cueing system operates both with robotic devices, as well as humans, to dynamically adjust voice or audio characteristics, such as loudness, modulation, pitch, tone, etc., and sounds. The automatic cueing system may directly or indirectly control the robotic devices, and may provide visual and/or audio cues to the humans, in order to enhance their interaction with other humans.

In one example, the automatic cueing system controls the robotic devices and their communication with humans, such as patients in a hospital setting. The voice or audio characteristics and sounds of the robotic devices can be dynamically adjusted in real-time in order to ensure the stability and comfort of the patients.

In another example, the automatic cueing system provides visual and/or audio cues to the humans, such as employees of a healthcare call center, regarding their communication with other humans, such as patients or customers. The visual and/or audio cues remind the healthcare call center employees to adjust their voice characteristics dynamically when speaking to the patients or customers.

The result is that the automatic cueing system helps protect the patient's health condition, both mentally and physically. The automatic cueing system also helps increase the patient's or customer's satisfaction when they interact with robotic devices or seek consultations from the healthcare call centers.

Cloud Computing Environment

Figure 1:
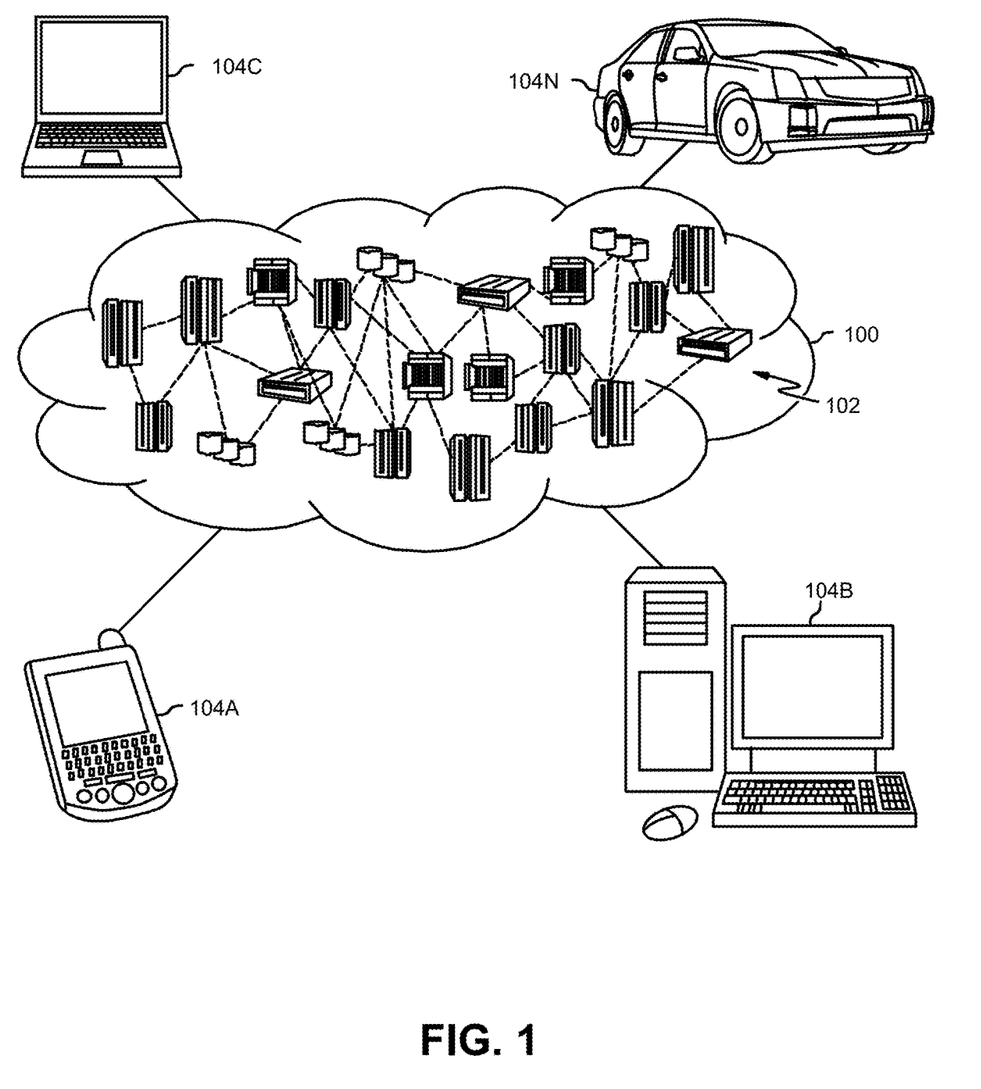
FIG. 1 is a pictorial representation of an illustrative cloud computing environment used for implementing an automatic cueing system for real-time communication, according to one embodiment.

FIG. 1 is a pictorial representation of an illustrative cloud computing environment 100 used for implementing the automatic cueing system for real-time communication, according to one embodiment.

As shown, a cloud computing environment 100 includes one or more cloud computing nodes 102 with which local computing devices used by cloud consumers, such as, for example, personal digital assistant (PDA) or cellular telephone 104A, desktop computer 104B, laptop computer 104C, and/or automobile computer system 104N may communicate. Nodes 102 may communicate with one another. They may be grouped (not shown) physically or virtually, in one or more networks, such as Private, Community, Public, or Hybrid clouds, or a combination thereof. This allows cloud computing environment 100 to offer infrastructure, platforms and/or software as services for which a cloud consumer does not need to maintain resources on a local computing device. It is understood that the types of computing devices 104A-N shown in FIG. 1 are intended to be illustrative only and that computing nodes 102 and cloud computing environment 100 can communicate with any type of computerized device over any type of network and/or network addressable connection (e.g., using a web browser).

The computing nodes 102 and/or computing devices 104A-N perform various functions and steps as described in more detail below.

System Description

Figure 2:
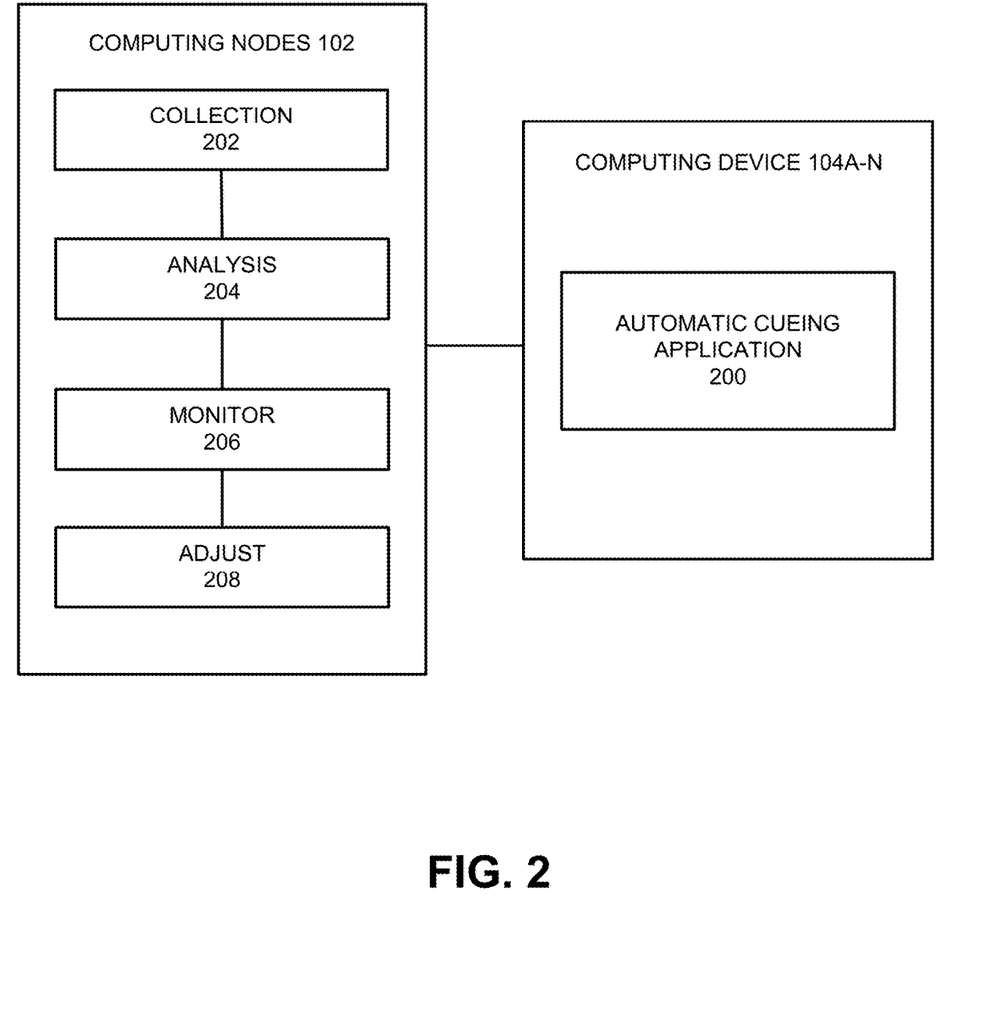
FIG. 2 is a block diagram illustrating how the system and method for automatic cueing for real-time communication is implemented, according to one embodiment.

FIG. 2 is a block diagram illustrating how the system and method for automatic cueing for real-time communication is implemented, according to one embodiment. In this embodiment, the system and method are implemented by:

during a verbal interaction with a first person (e.g., a patient or customer), a second person (e.g., an employee of a healthcare call center) and/or a robotic device invokes an automatic cueing application 200 on the computing device 104A-N, wherein the robotic device itself may incorporate the computing device 104A-N; and the computing nodes 102 perform a plurality of steps or functions 202-208 that accept a command from the computing device 104A-N to initiate the automatic cueing system and then perform the automatic cueing system.

There are a number of prerequisites to the computing nodes 102 performing the automatic cueing system, such as obtaining information on the first person. For example, the computing nodes 102 must be able to access the first person's profile data with their agreement and in compliance with HIPAA (Health Insurance Portability and Accountability Act of 1996) requirements that provides data privacy and security provisions for safeguarding medical information.

In a Collection step or function 202, the computing nodes 102 perform the step or function of collecting the first person's profile data, which may include information on how the first person reacts to different voice or audio characteristics and sounds, as well as a medical history of the first person.

In an Analysis step or function 204, the computing nodes 102 perform the step or function of analyzing the first person's voice or audio characteristics and sounds to categorize a current condition of the first person. The computing nodes 102 may combine this analysis with other information, such as the first person's vital signs and medical history, to categorize a current condition of the first person. The categorization of the current condition of the first person may include determining a state and/or sentiment of the first person, such as normal (e.g., calm, happy, etc.) or abnormal (e.g., excited, upset, etc.).

In the Analysis step or function 204, the computing nodes 102 also perform the step or function of analyzing the voice or audio characteristics and sounds of responses made by the second person and/or the robotic device to the first person.

In a Monitor step or function 206, the computing nodes 102 perform the step or function of continuously monitoring the voice or audio characteristics and sounds of the first person, as well as the voice or audio characteristics and sounds of the responses made by the second person and/or the robotic device. The computing nodes 102 also may perform the step or function of continuously monitoring the first person's vital signs to update the current condition of the first person. The computing nodes 102 may use this monitoring to determine whether any changes to the state and/or sentiment of the first person have occurred, in order to optimize their interaction with the second person and/or robotic device.

In an Adjust step or function 208, the computing nodes 102 perform the step or function of dynamically adjusting the voice or audio characteristics and sounds of the responses made by the second person and/or the robotic device, based on the first person's profile data and the current condition of the first person, to ensure that the current condition of the first person stays within a desired range. In this regard, the computing nodes 102 directly or indirectly control the robotic device to dynamically adjust the voice or audio characteristics and sounds of the responses made by the robotic device. Similarly, the computing nodes 102 provide visual and/or audio cues to the second person to dynamically adjust the voice or audio characteristics and sounds of the responses made by the second person.

These steps 202-208 may be repeated as necessary, and any one or more of the steps 202-208 may be omitted as required.

Use Cases

Consider the following use cases where the cloud computing environment 100 is used for providing automatic cueing for real-time communication.

A first example concerns a patient named John:

John has an unstable blood pressure issue. He tends to have elevated blood pressure when he talks to people using a loud voice.

The computing nodes 102 detect that John has such a condition by evaluating his profile data.

The computing nodes 102 are aware that John has just checked into the ER, because he has been experiencing some dizziness.

The ER includes a robotic device that checks John's condition and obtains initial information by talking to John. The robotic device is integrated with the cloud computing environment 100.

The computing nodes 102 analyze John's voice or audio characteristics and sounds, and determine his state or sentiment from his voice or audio characteristics and sounds.

The computing nodes 102 adjust the voice or audio characteristics and sounds of the responses made by the robotic device, to ensure that it does not trigger any more discomfort from John. This helps John's blood pressure to be maintained at a stable level.

The computing nodes 102 continue to analyze John' voice or audio characteristics and sounds, and update his state or sentiment from his voice or audio characteristics and sounds.

A second example concerns a patient named Mary:

Mary makes a call to a healthcare call center. The healthcare call center has a call monitoring system that is integrated with the cloud computing environment 100.

Mary tends to get more anxious when she has to describe her symptoms to an employee of the healthcare call center, because she is already not feeling well.

The computing nodes 102 analyze Mary's voice or audio characteristics and sounds, and determine her state or sentiment from the voice or audio characteristics and sounds.

The computing nodes 102 generates visual and/or audio cues for the employee of the healthcare call center to dynamically adjust their voice or audio characteristics and sounds to reduce Mary's anxiety during the interaction.

The computing nodes 102 continue to analyze Mary's voice or characteristics and sounds, and update her state or sentiment from her voice or audio characteristics and sounds.

The computing nodes 102 can also provide additional intervention during the interaction between Mary and the employee of the healthcare call center as needed. For example, the computing nodes 102 can inform Mary that they highly value her feedback and they can also find another employee to assist her better.

Statutory Subject Matter

It can be seen that the present invention provides a number of benefits and advantages. These benefits and advantages include improvements to the technology or technical field of health care, patient interaction and call centers, and more specifically, providing for an automatic cueing system for real-time communication. These benefits and advantages also include improvements to the functioning of the devices themselves, including the cloud computing environment 100 generally and the computing nodes 102 specifically, as well as the computing devices 104A-N, as compared to prior computer-implemented methods and systems providing robotic device control and/or call center systems.

Figure 3:
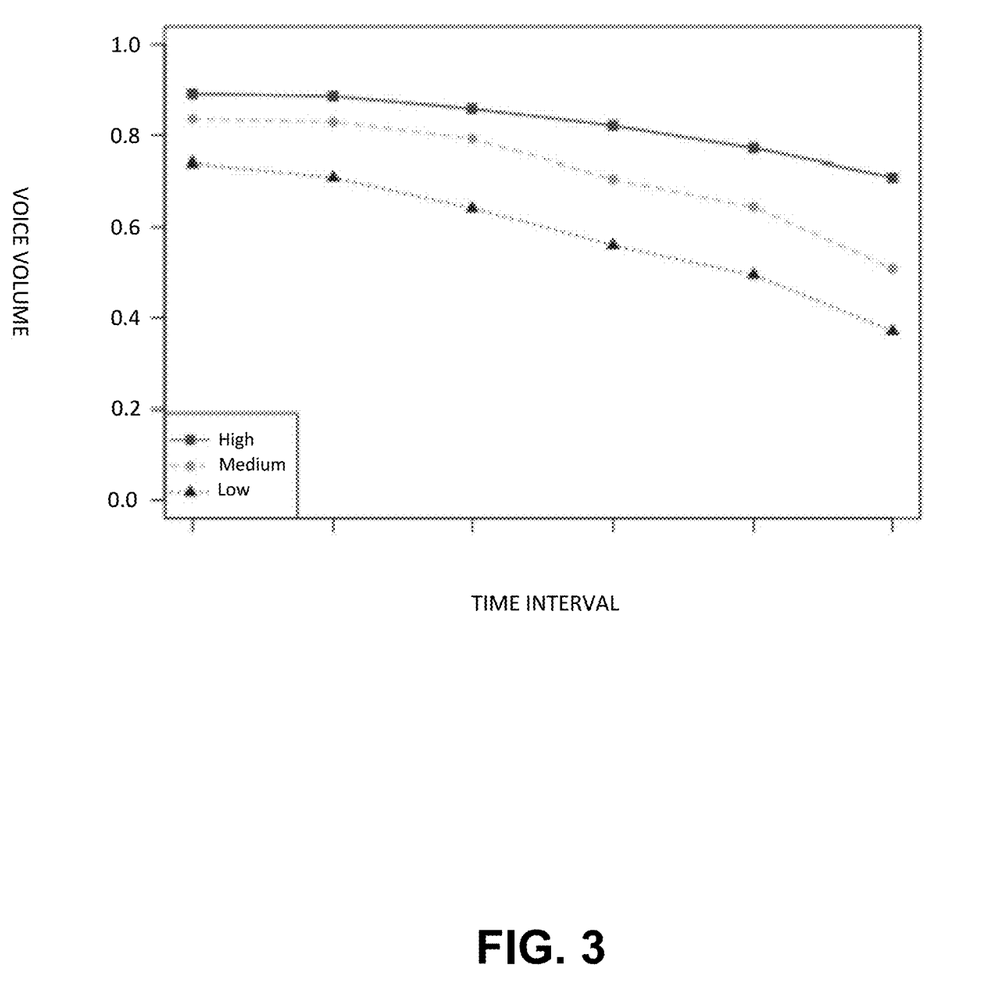
FIG. 3 is an image illustrating a visual cue displayed by the automatic cueing system, according to one embodiment.

With regard to improvements to the technologies or technical fields of health care, patient interaction and call centers, one example of the results of the automatic cueing for real-time communication is shown in FIG. 3. Specifically, FIG. 3 shows a graph of voice volume vs. time interval, with three different plots of high, medium and low voice volumes. In each plot, the voice volumes decrease over the time interval as the automatic cueing system dynamically adjusts the voice or audio characteristics and sounds of the responses made to the first person. This indicates that the automatic cueing system reduces stress and tension in the interaction of patients and customers with the healthcare call center and/or robotic device.

Both generally and specifically, these steps and functions of the computer-implemented method and system comprise specific improvements other than what is well-understood, routine and conventional in the field. Moreover, these steps and functions of the computer-implemented method and system add unconventional steps to a particular useful application.

Cloud Computing

It is to be understood that this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring again to FIG. 1, illustrative cloud computing environment 100 is depicted. As shown, cloud computing environment 100 includes one or more cloud computing nodes 102 with which local computing devices used by cloud consumers, such as, for example, personal digital assistant (PDA) or cellular telephone 104A, desktop computer 104B, laptop computer 104C, and/or automobile computer system 104N may communicate. Nodes 102 may communicate with one another. They may be grouped (not shown) physically or virtually, in one or more networks, such as Private, Community, Public, or Hybrid clouds as described hereinabove, or a combination thereof. This allows cloud computing environment 100 to offer infrastructure, platforms and/or software as services for which a cloud consumer does not need to maintain resources on a local computing device. It is understood that the types of computing devices 104A-N shown in FIG. 1 are intended to be illustrative only and that computing nodes 102 and cloud computing environment 100 can communicate with any type of computerized device over any type of network and/or network addressable connection (e.g., using a web browser).

Figure 4:
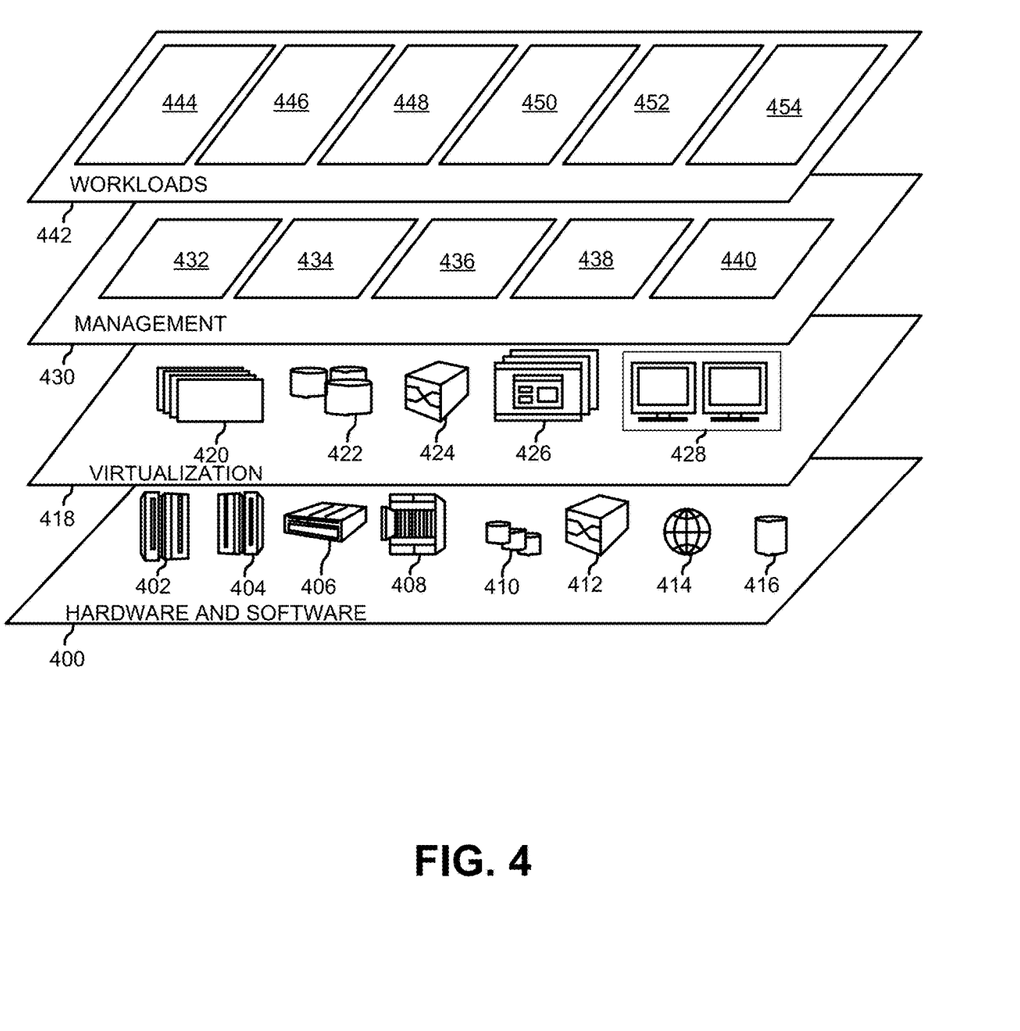
FIG. 4 illustrates a set of functional abstraction layers provided by the cloud computing environment.

Referring now to FIG. 4, a set of functional abstraction layers provided by cloud computing environment 100 (FIG. 1) is shown. It should be understood in advance that the components, layers, and functions shown in FIG. 4 are intended to be illustrative only and embodiments of the invention are not limited thereto. As depicted, the following layers and corresponding functions are provided:

Hardware and software layer 400 includes hardware and software components. Examples of hardware components include: one or more computers such as mainframes 402; RISC (Reduced Instruction Set Computer) architecture based servers 404; servers 406; and blade servers 408; storage devices 410; and networks and networking components 412. In some embodiments, software components include network application server software 414 and database software 416.

Virtualization layer 418 provides an abstraction layer from which the following examples of virtual entities may be provided: virtual servers 420; virtual storage 422; virtual networks 424, including virtual private networks; virtual applications and operating systems 426; and virtual clients 428.

In one example, management layer 430 may provide the functions described above. Resource provisioning 432 provides dynamic procurement of computing resources and other resources that are utilized to perform tasks within the cloud computing environment 100. Metering and pricing 434 provide cost tracking as resources are utilized within the cloud computing environment 100, and billing or invoicing for consumption of these resources. In one example, these resources may include application software licenses. Security provides identity verification for cloud consumers and tasks, as well as protection for data and other resources. User portal 436 provides access to the cloud computing environment 100 for consumers and system administrators. Service level management 438, which includes containers, provides cloud computing resource allocation and management such that required service levels are met. Service Level Agreement (SLA) planning and fulfillment 440 provide pre-arrangement for, and procurement of, cloud computing resources for which a future requirement is anticipated in accordance with an SLA.

Workloads layer 442 provides examples of functionality for which the cloud computing environment 100 may be utilized. Examples of workloads, tasks and functions which may be provided from this layer include: mapping and navigation 444; software development and lifecycle management 446; virtual classroom education delivery 448; data analytics processing 450; transaction processing 452; etc. More specifically, this layer includes the workloads, tasks and functions for providing an automatic cueing system for real-time communication 454 as described above.

Computer Program Product

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart illustrations and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart illustrations and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart illustrations and/or block diagram block or blocks.

The flowchart illustrations and block diagrams in the Figures illustrate the architecture, functionality, and operation of possible implementations of systems, methods, and computer program products according to various embodiments of the present invention. In this regard, each block in the flowchart illustrations or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts or carry out combinations of special purpose hardware and computer instructions.

CONCLUSION

This concludes the description of the various embodiments of the present invention. The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein. Since many embodiments of the invention can be made without departing from the spirit and scope of the invention, the invention resides in the claims hereinafter appended.

What is claimed is:

1. A computer-implemented method, comprising:
providing an automatic cueing system for real-time communication with a first person, by:
collecting the first person's profile data to determine how the first person reacts to different voice or audio characteristics and sounds, wherein determining a reaction of the first person is based on a known change or a currently detected change in a condition of the first person in response to voice or audio characteristics and sounds;
analyzing the first person's voice or audio characteristics and sounds to categorize a current condition of the first person; and
dynamically adjusting voice or audio characteristics and sounds of responses made to the first person, based on the first person's profile data and the current condition of the first person.

2. The method of claim 1, further comprising continuously monitoring the first person's voice or audio characteristics and sounds.

3. The method of claim 1, wherein the automatic cueing system dynamically adjusts the voice or audio characteristics and sounds of the responses made to the first person, to ensure that the current condition of the first person stays within a desired range.

4. The method of claim 1, wherein the automatic cueing system directly or indirectly controls at least one robotic device to dynamically adjust the voice or audio characteristics and sounds of the responses made by the robotic device to the first person.

5. The method of claim 4, further comprising continuously monitoring the voice or audio characteristics and sounds of the responses made by the robotic device to the first person.

6. The method of claim 1, wherein the automatic cueing system provides visual and/or audio cues to a second person to dynamically adjust the voice or audio characteristics and sounds of the responses made by the second person to the first person.

7. The method of claim 6, further comprising continuously monitoring the voice or audio characteristics and sounds of the responses made by the second person to the first person.

8. The method of claim 1, wherein the first person's profile data includes a medical history of the first person.

9. The method of claim 8, further comprising continuously monitoring the first person's vital signs to update the current condition of the first person.

10. A computer-implemented system, comprising:
one or more computers programmed for providing an automatic cueing system for real-time communication with a first person, by:
collecting the first person's profile data to determine how the first person reacts to different voice or audio characteristics and sounds, wherein determining a reaction of the first person is based on a known change or a currently detected change in a condition of the first person in response to voice or audio characteristics and sounds;
analyzing the first person's voice or audio characteristics and sounds to categorize a current condition of the first person; and
dynamically adjusting voice or audio characteristics and sounds of responses made to the first person, based on the first person's profile data and the current condition of the first person.

11. The system of claim 10, further comprising continuously monitoring the first person's voice or audio characteristics and sounds.

12. The system of claim 10, wherein the automatic cueing system dynamically adjusts the voice or audio characteristics and sounds of the responses made to the first person, to ensure that the current condition of the first person stays within a desired range.

13. The system of claim 10, wherein the automatic cueing system directly or indirectly controls at least one robotic device to dynamically adjust the voice or audio characteristics and sounds of the responses made by the robotic device to the first person.

14. The system of claim 13, further comprising continuously monitoring the voice or audio characteristics and sounds of the responses made by the robotic device to the first person.

15. The system of claim 10, wherein the automatic cueing system provides visual and/or audio cues to a second person to dynamically adjust the voice or audio characteristics and sounds of the responses made by the second person to the first person.

16. The system of claim 15, further comprising continuously monitoring the voice or audio characteristics and sounds of the responses made by the second person to the first person.

17. The system of claim 10, wherein the first person's profile data includes a medical history of the first person.

18. The system of claim 17, further comprising continuously monitoring the first person's vital signs to update the current condition of the first person.

19. A computer program product, the computer program product comprising a computer readable storage medium having program instructions embodied therewith, the program instructions executable by one or more computers to cause the computers to perform a method, comprising:
providing an automatic cueing system for real-time communication with a first person, by:
collecting the first person's profile data to determine how the first person reacts to different voice or audio characteristics and sounds, wherein determining a reaction of the first person is based on a known change or a currently detected change in a condition of the first person in response to voice or audio characteristics and sounds;
analyzing the first person's voice or audio characteristics and sounds to categorize a current condition of the first person; and
dynamically adjusting voice or audio characteristics and sounds of responses made to the first person, based on the first person's profile data and the current condition of the first person.

20. The computer program product of claim 19, wherein the automatic cueing system:
directly or indirectly controls at least one robotic device to dynamically adjust the voice or audio characteristics and sounds of the responses made by the robotic device to the first person; or
provides visual and/or audio cues to a second person to dynamically adjust the voice or audio characteristics and sounds of the responses made by the second person to the first person.

* * * * *